United States Patent [19]

Rothgery et al.

[11] Patent Number: 4,800,232
[45] Date of Patent: Jan. 24, 1989

[54] PROCESS FOR PRODUCING TRIAMINOGUANIDINE NITRATE AND THE HIGH MELTING POINT PRODUCT SO PRODUCED

[75] Inventors: Eugene F. Rothgery, North Branford; Steven A. Manke, Wallingford, both of Conn.

[73] Assignee: Olin Corporation, Cheshire, Conn.

[21] Appl. No.: 109,010

[22] Filed: Oct. 16, 1987

[51] Int. Cl.$^4$ ............................................. C07C 133/10
[52] U.S. Cl. .................................................. 564/227
[58] Field of Search ......................................... 564/227

[56] References Cited

U.S. PATENT DOCUMENTS

| | | | |
|---|---|---|---|
| 3,285,958 | 11/1966 | Satriana | 260/564 |
| 3,813,439 | 5/1974 | Picard et al. | 260/564 |
| 3,950,421 | 4/1976 | Haury | 260/564 |

FOREIGN PATENT DOCUMENTS

| | | | |
|---|---|---|---|
| 1518197 | 9/1979 | Fed. Rep. of Germany | 564/227 |
| 3341645 | 5/1985 | Fed. Rep. of Germany | 564/227 |
| 61-236761 | 10/1986 | Japan | 564/227 |

*Primary Examiner*—James H. Reamer
*Attorney, Agent, or Firm*—Dale Lynn Carlson

[57] ABSTRACT

A process for producing triaminoguanidine nitrate, and, more specifically, a process which involves reacting hydrazine, nitric acid and cyanamide in specified molar ratios. Also claimed is the high melting point product so produced.

3 Claims, No Drawings

PROCESS FOR PRODUCING TRIAMINOGUANIDINE NITRATE AND THE HIGH MELTING POINT PRODUCT SO PRODUCED

FIELD OF THE INVENTION

This invention relates generally to a process for producing triaminoguanidine nitrate, and, more specifically, to such a process which involves reacting hydrazine, hydrazine nitrate and cyanamide in a molar ratio of reactants selected to provide product in a high yield and purity. Also claimed is the high melting point product produced by this process.

BACKGROUND OF THE INVENTION

A conventional commercial process for producing triaminoguanidine nitrate (TAGN) involves the reaction of guanidine nitrate with hydrazine in an aqueous nitrate medium. This process is disclosed in U.S. Pat. No. 3,950,421 as providing product yields of about 80 percent. However, the guanidine nitrate is generally prepared from cyanamide in a time consuming and costly reaction.

A direct process for producing TAGN in high yield by reacting cyanamide, hydrazine nitrate, and hydrazine is disclosed in German Auslegeschrift No. 1,518,197, assigned to Wasag-Chemie A.G. This Auslegeschrift discloses a molar ratio of these reactants of 1 to 1 to 2, respectively, to provide a high TAGN yield of about 80 percent based on the amount of cyanamide reactant employed. Although this product yield is excellent, the product purity, based upon the product melting point of 206° C. disclosed in the Auslegeschrift, is something less than is now frequently required in the industry.

Accordingly, a new process for producing TAGN, in high yield and improved purity using a cyanamide reactant would be highly desirable from a commercial standpoint.

SUMMARY OF THE INVENTION

In one aspect, the present invention relates to a process for producing triaminoguanidine nitrate by reacting an aqueous mixture of cyanamide, hydrazine nitrate, and hydrazine in a molar ratio of between about 1:2:1 and about 1:4:4 to provide a product having a melting point of at least 210° C., preferably at least 220° C.

In another aspect, the present invention relates to the high melting point product produced by the above process.

DETAILED DESCRIPTION OF THE INVENTION

In the process of the present invention an aqueous mixture of cyanamide, hydrazine nitrate, and hydrazine are reacted. The simplified equation for this reaction is as follows:

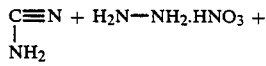

-continued

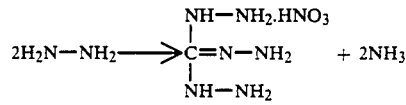

It has now been surprisingly found that the process of the present invention provides an enhanced product purity relative to the prior art, as measured by an increased product melting point as compared to the melting product produced by prior art processes.

Without wishing to be bound by any particular theory, it is speculated by the present inventors that the efficacy of the present process in providing high purity TAGN product is attributable, at least in part, to the desired product-stabilizing effect of the presence of a molar excess of hydrazine nitrate reactant relative to the amount of cyanamide reactant employed. The excess nitrate ion produced in the reaction mixture via the use of a molar excess of hydrazine nitrate insures that all of the TAG will be neutralized to the nitrate salt rather than the more unstable TAG base which is subject to decomposition to form undesirable by-products.

The reaction to produce TAGN in accordance with the process of the present invention is preferably conducted at reflux temperature (typically 100° C.-110° C., preferably 103° C.-105° C.) and atmospheric pressure.

Although the order of addition of the reactants to the reactor can be selected as desired, it is preferred to add aqueous hydrazine to an aqueous mixture of hydrazine nitrate and cyanamide. The appearance of an exotherm upon addition of the aqueous hydrazine signals the reaction taking place.

In order to insure a complete reaction, the reaction mixture is typically refluxed for up to two hours or longer. The reaction mixture is then cooled (preferably to 10° C.) and filtered to provide a filtrate and a white precipitate. The white precipitate is washed (preferably with methanol) and dried to provide a white TAGN product in solid form. The filtrate can then be recycled into a reaction mixture for continuous processing to TAGN.

The purity of the TAGN product produced in accordance with the present process is very high, based upon the observed melting point thereof. The process provides TAGN product having a melting point of at least 210° C., preferably at least 220° C. The TAGN yield is typically between 70 percent and 85 (preferably between 75 and 85) percent of theoretical.

The TAGN product of the present invention is useful as a burn-rate modifier for gun propellants. This TAGN product has excellent storage stability and is suitable for long-term storage prior to use thereof.

The following example is intended to illustrate, but in no way limit, the present invention.

EXAMPLE 1

Preparation of TAGN Using the Preferred Molar Ratios of Reactants

To a nitrogen purged flask was added: water in an amount of 50 g, a 64 percent aqueous hydrazine solution in an amount of 37.5 g (0.75 mole), and a 70 percent nitric acid in an amount of 67.5 g (0.75 mole) while cooling. The solution of hydrazine nitrate was cooled to 30° C. (pH at this point was 7.0) and a 50 percent aqueous solution of cyanamide added in an amount of 21 g (0.25 mole). No exotherm was noted. Aqueous hydrazine in an amount of 37.5 g (0.75 mole) was added and the mixture exothermed to a temperature of 45° C. The mixture was refluxed two hours, causing ammonia gas to evolve. On cooling to 10° C., a white precipitate formed. Filtration provided 157.6 g of filtrate, which was recycled. The precipitate was washed with methanol and dried to give 32.3 g of product melting at between 220.8°–224.6° C., in a 77.4 percent yield.

EXAMPLE 2 AND COMPARATIVE EXAMPLES A AND B

Comparison of Preparations of TAGN Using Various Molar Ratios of Reactants

Following the procedure of EXAMPLE 1, additional preparations of TAGN were made with the molar ratio of reactants being selected as given in TABLE I below. The TAGN yield and product melting point for these reactions is also given in TABLE I.

TABLE I

| | Comparison of Ratios Molar Ratio of Reactants | | | | |
|---|---|---|---|---|---|
| Example | Cyan-amide | Hydrazine Nitrate | Hydra-zine | Product Yield | Product Melting Point (°C.) |
| 1 | 1.0 | 3.0 | 3.0 | 77.4 | 221–225 |
| 2 | 1.0 | 4.0 | 2.0 | 71.8 | 215–217 |
| Comparative A | 1.0 | 6.0 | 0 | 68.4 | 190–203 |
| Comparative B | 1.0 | 1.1 | 2.2 | 40.7 | 213–216 |

The results with respect to TAGN yield and product melting point as provided in TABLE I demonstrate the advantages associated with using a molar ratio of reactants within the scope of the present invention. Note that EXAMPLE 1 provides both a high TAGN yield of 77.4 percent and product melting point of 221°–225°. EXAMPLE 1 utilizes the preferred molar ratio of reactants of cyanamide to hydrazine nitrate to hydrazine of 1:3:3. A less preferred molar ratio of reactants is provided in EXAMPLE 2, namely a cyanamide to hydrazine nitrate to hydrazine ratio of 1:4:2. This less preferred ratio provided a good product yield of 71.8 percent and product melting point of 215°–217° C.

In contrast to these examples, Comparative Examples A and B employed a molar ratio of reactants outside the scope of the present invention. Note that Comparative Example A utilized no free hydrazine reactant, provided a decreased yield of 68.4 percent and an unacceptable product melting point of 190°–203° C. Likewise, Comparative Example B, employing a molar ratio of reactants of cyanamide to hydrazine nitrate to hydrazine of 1.0:1.1:2.2, provided an unacceptable product yield of 40.7 percent, although the product melting point of 213°–216° C. fell within the acceptable range.

What is claimed is:

1. A process for producing triaminoguanidine nitrate by a reaction of an aqueous mixture of cyanamide, hydrazine nitrate, and hydrazine in a molar ratio of between about 1:2:1 and about 1:4:4 to provide a product having a melting point of at least 220° C.

2. The process of claim 1 wherein said reaction is conducted at reflux temperature and atmospheric pressure.

3. The process of claim 1 wherein said molar ratio is 1:3:3.

* * * * *